(12) United States Patent
Cotte et al.

(10) Patent No.: US 8,304,550 B2
(45) Date of Patent: Nov. 6, 2012

(54) PROCESS FOR THE CATALYTIC SYNTHESIS OF DIARYL ETHERS

(75) Inventors: Alain Cotte, Leverkusen (DE); Nikolaus Muller, Wallhausen (DE); Matthias Gotta, Cologne (DE); Matthias Beller, Ostseebad Nienhagen (DE); Thomas Schareina, Cammin (DE); Alexander Zapf, Rosenheim (DE)

(73) Assignee: Saltigo GmbH, Langenfeld (DE)

( * ) Notice: Subject to any disclaimer, the term of this patent is extended or adjusted under 35 U.S.C. 154(b) by 703 days.

(21) Appl. No.: 12/275,316

(22) Filed: Nov. 21, 2008

(65) Prior Publication Data

US 2009/0143594 A1 Jun. 4, 2009

(30) Foreign Application Priority Data

Nov. 30, 2007 (EP) .................................... 07122010

(51) Int. Cl.
*C07D 213/63* (2006.01)
*C07C 209/00* (2006.01)
*C07C 41/01* (2006.01)
*B01J 31/18* (2006.01)

(52) U.S. Cl. ......... 546/290; 502/165; 564/395; 568/635

(58) Field of Classification Search .................. None
See application file for complete search history.

(56) References Cited

U.S. PATENT DOCUMENTS 4,404,359 A * 9/1983 Naarmann et al. ............ 528/216

OTHER PUBLICATIONS

Chauhan, SMS. et al. Copper(I) chloride catalyzed synthesis of diaryl ethers in ionic liquids under mild conditions. Synthetic Communications. 2003, vol. 33(20), p. 3607-3614.*
Chauhan, SMS. et al. Copper(I) chloride catalyzed synthesis of diaryl ethers in ionic liquids under mild conditions. Synthetic Communications. 2003. vol. 33(20), p. 3607-3614.*
Beller, M. et al. A State-of-the-Art Cyanation of Aryl Bromides: A Novel and Versatile Copper Catalyst System Inspired by Nature. Chemistry—A European Journal. 2007, vol. 13(21), p. 6251.*
J. Lindley, *Tetrahedron* 1984, 40, 1433-1456.
J. F. Hartwig, *Angew. Chem. Int. Ed.*, 1998, 37, 2047-2067.
S. Harkal, K. Kumar, D. Michalik, A. Zapf, R. Jackstell, F. Rataboul, T. Riermeier, A. Monsees, M. Beller, *Tetrahedron Lett.* 2005, 46, 3237-3240.
E. Buck, Z. J. Song, D. Tschaen, P. G. Dormer, R. P. Volante, P. J. Reider, *Org. Lett.* 2002, 4, 1623-1626.
Q. Cai, B. L. Zou, D. W. Ma, *Angew. Chem. Int. Edit.* 2006, 45, 1276-1279.
P. J. Fagan, E. Hauptman, R. Shapiro, A. Casalnuovo, *J. Am. Chem. Soc.* 2000, 122, 5043-5051.
R. Hosseinzadeh, M. Tajbakhsh, M. Mohadjerani, M. Alikarami, *Synlett* 2005, 1101-1104.
H.-J. Cristau, P. P. Cellier, S. Hamada, J.-F. Spindler, M. Taillefer, *Org. Lett.* 2004, 6, 913-916.
A. V. Kalinin, J. F. Bower, P. Riebel, V. Snieckus, *J. Org. Chem.* 1999, 64, 2986-2987.
J. F. Marcoux, S. Doye, S. L. Buchwald, *J. Am. Chem. Soc.* 1997, 119, 10539-10540.
R. Gujadhur, D. Venkataraman, *Synth. Commun.* 2001, 31, 2865-2879.
R. K. Gujadhur, C. G. Bates, D. Venkataraman, *Org. Lett.* 2001, 3, 4315-4317.
L.-W. Xu, C.-G. Xia, J.-W. Li, X.-X. Hu, *Synlett* 2003, 2071-2073.
R. F. P. Comdom, M. L. D. Palacios, *Synth. Commun.* 2003, 33, 921-926.
Y. T. Luo, J. X. Wu, R. X. Ren, *Synlett* 2003, 1734-1736.
Y. Jin, J. Y. Liu, Y. W. Yin, H. Fu, Y. Y. Jiang, Y. F. Zhao, *Synlett* 2006, 1564-1568.
T. Miao, L. Wang, *Tetrahedron Lett.*, 2007, 48, 95-99.
B. H. Lipshutz, J. B. Unger, B. R. Taft, *Org. Lett.* 2007, 9, 1089-1092.
A. Wang, R. S. Zeng, H. Q. Wei, A. Q. Jia, J. P. Zou, *Chin. J. Chem.*, 2006, 24, 1062-1065.
R. A. Widenhoefer, H. A. Zhong, S. L. Buchwald, *J. Am. Chem. Soc.*, 1997, 119, 6787-6795.

* cited by examiner

*Primary Examiner* — Kamal Saeed
(74) *Attorney, Agent, or Firm* — Michael A. Miller

(57) ABSTRACT

Described is a process for preparing diaryl ethers of the formula (I)

Ar—O—Ar'  (I)

In which Ar is an aryl or substituted aryl group and Ar' is an aryl, substituted aryl, heteroaryl or substituted heteroaryl group,
by reacting an aryl of formula (II) or a aryloxy salt of formula (III)

Ar—OH  (II)

Ar—OR  (III)

In which Ar has the same meaning as in formula (I) and R is an alkali metal,
with an aryl or heteroaryl bromide of formula (IV)

Ar'—Br  (IV)

In which Ar' has the same meaning as in formula (I),
characterized in that the reaction is carried out in the presence of a copper(I)salt and a 1-substituted imidazole as catalyst system.

10 Claims, No Drawings

PROCESS FOR THE CATALYTIC SYNTHESIS OF DIARYL ETHERS

The present invention relates to an advantageous process for the catalytic synthesis of diaryl ethers.

For a long time, the Ullmann coupling was the method of choice for the preparation of diaryl ethers. Large, usually overstoichiometric quantities of copper or copper salts, an excess of phenol and high temperatures were used to convert aryl halides into the corresponding diaryl ethers (J. Lindley, Tetrahedron 1984, 40, 1433-1456).

An improved method was introduced applying palladium catalysts in the late 90's (e.g. J. F. Hartwig, Angew. Chem. Int. Ed., 1998, 37, 2047-2067; R. A. Widenhoefer, H. A. Zhong, S. L. Buchwald, J. Am. Chem. Soc., 1997, 119, 6787-6795). Although the procedures have been further optimized during the next years (e.g. S. Harkal, K. Kumar, D. Michalik, A. Zapf, R. Jackstell, F. Rataboul, T. Riermeier, A. Monsees, M. Beller, Tetrahedron Lett. 2005, 46, 3237-3240), a common drawback of all palladium-catalyzed reactions is price of the catalyst metal and the need for often expensive phosphine ligands.

Attempts to improve the classical copper-mediated Ullmann coupling reaction aim at rendering the reaction catalytic, with reduced copper content at lower temperatures, by varying the base, solvents and especially the use of ligands.

Song and co-workers (E. Buck, Z. J. Song, D. Tschaen, P. G. Dormer, R. P. Volante, P. J. Reider, Org. Lett. 2002, 4, 1623-1626) reported that 2,2,6,6-tetramethylheptane-3,5-dione can be applied as a suitable ligand for coupling various aryl bromides with phenols. This modification brought significant improvements to reactions which usually do not work well with the classical procedure of the Ullmann diaryl ether synthesis, e.g. in case of coupling reactions of aryl halides possessing electron-donating groups with phenols possessing electron-withdrawing groups. However, phenols with strong electron-withdrawing groups did not undergo the desired ether formation and phenols with ortho-methoxy and -acetoxy groups reacted slowly.

Cai et al. (Q. Cai, B. L. Zou, D. W. Ma, Angew. Chem. Int. Edit. 2006, 45, 1276-1279) described a very efficient ligand, N,N-dimethylglycine, for acceleration of the Ullmann diaryl ether synthesis.

The application of this ligand allows the reaction to be performed in dioxane at 90° C., which is a very low temperature for Ullmann diaryl ether coupling. Both electron-rich and electron-poor aryl halides are suitable substrates for this reaction and provide the corresponding diaryl ethers in good to excellent yields. Steric hindrance in both aryl halides and phenols slightly disfavored the reaction. However, when higher temperature and higher catalyst and ligand loading were applied, this obstacle was overcome. For example, in the reaction of sterically hindered 2-bromotoluene with 4-methoxyphenol, good yields were obtained by raising the reaction temperature to 105° C. L-Proline was also reported to be an effective additive for acceleration of the reaction.

Another contribution in this respect was made by Hauptman and co-workers (P. J. Fagan, E. Hauptman, R. Shapiro, A. Casalnuovo, J. Am. Chem. Soc. 2000, 122, 5043-5051) who systematically investigated different ligands by 'intelligent/random library screening' of a broad range of mono-, bi- and tridendate pyridine-containing ligands in the copper-catalysed coupling of 2-bromo-4,6-dimethylaniline with sodium phenolate. It turned out that in diglyme or dimethoxyethane, the use of bidendate chelators with small 'biteangles', especially 2-aminopyridine and 8-hydroxyquinoline, was most successful and provided better yields with lower amounts of reduced arene by-product. On the other hand, the most effective ligands did not work well in other solvents, suggesting the complexity of this reaction.

Hosseinzadeh et al. (R. Hosseinzadeh, M. Tajbakhsh, M. Mohadjerani, M. Alikarami, Synlett 2005, 1101-1104) reported an improvement in the synthesis of diaryl ethers from phenols and aryl iodides (X=I) in the presence of copper(I) iodide using 1,10-phenanthroline as a ligand and potassium fluoride supported on aluminum oxide as a base.

Among the best ligands in copper-mediated diaryl ether synthesis to date are the multidentate N— donors Chxn-Py-Al, salicylaldoxime (Salox) and dimethylglyoxime (DMG) described by Cristau et al. (H.-J. Cristau, P. P. Cellier, S. Hamada, J.-F. Spindler, M. Taillefer, Org. Lett. 2004, 6, 913-916). The reaction was carried out in acetonitrile at 80° C., which is one of the lowest temperatures used in the Ullmann diaryl ether synthesis, with copper(I) oxide as pre-catalyst. Aryl iodides showed higher reactivity compared to aryl bromides. High yields (80-100%) of diaryl ethers were also obtained when the reaction was carried out in DMF at 110° C. The method was effective as well for coupling of sterically hindered o-cresol and 2-iodotoluene. The major drawback of this method was its inability to couple electron-poor phenols.

Other authors tried to improve the Ullmann diaryl ether synthesis by modifying a catalyst, instead of adding a ligand, in order to achieve enhanced catalyst solubility. A new variation was reported by Snieckus and co-workers (A. V. Kalinin, J. F. Bower, P. Riebel, V. Snieckus, J. Org. Chem. 1999, 64, 2986-2987), who employed $CuPF_6(MeCN)_4$ (5 mol %) rather than the air-labile $(CuOTf)_2.C_6H_6$ complex (J. F. Marcoux, S. Doye, S. L. Buchwald, J. Am. Chem. Soc. 1997, 119, 10539-10540) in refluxing toluene or xylenes in the presence of $Cs_2CO_3$ as base. The synthetic scope of this modification was established in the coupling of o-iodo- and o-bromo-benzamides and -benzenesulfonamides with phenols. In contrast to Buchwald's system ortho secondary and tertiary benzamides were well tolerated in the coupling process with a negligible difference in yields between iodides and bromides. E.g., N-ethyl-2-(m-tolyloxy)-benzamide was obtained in 88% yield from N-ethyl-2-iodobenzamide and m-cresol.

Gujadhur and Venkataraman reported the use of air- and moisture-stable $Cu(PPh_3)_3Br$ complex as a modified catalyst for the synthesis of diaryl ethers (R. Gujadhur, D. Venkataraman, Synth. Commun. 2001, 31, 2865-2879). The catalyst is soluble in most organic solvents and the reaction does not require any co-solvents. Using this method phenols can be coupled with electron-deficient aryl bromides such as 4-bromo-1-nitrobenzene and 4-bromobenzonitrile in N-methylpyrrolidinone. However, despite good yields (55-88%) in the coupling of electron-rich aryl bromides with electron-rich phenols, electron-deficient phenols could not be coupled.

The solubility of the copper catalyst can also be enhanced by the use of phenanthroline ligands. In R. K. Gujadhur, C. G. Bates, D. Venkataraman, Org. Lett. 2001, 3, 4315-4317 two air- and moisture-stable copper-phenanthroline complexes are described for the coupling of aryl bromides and phenols to form diaryl ethers in good yields (10 mol % Cu(neocup) $(PPh_3)Br$, $Cs_2CO_3$, toluene, 110° C., 36 h). However, yields of diaryl ethers were substantially lower for aryl bromides bearing ortho substituents (31% yields for coupling p-methylphenol with o-methylbromobenzene).

For coupling of o- and p-substituted phenols with inactivated aryl bromides and iodides, Xu et al. (L.-W. Xu, C.-G. Xia, J.-W. Li, X.-X. Hu, Synlett 2003, 2071-2073) reported a ligandless cross-coupling method using a Raney nickel-aluminum alloy, which participates in the formation of the reactive intermediate, thereby increasing the rate of its subsequent reaction. Various copper salts (e.g. CuCl, CuBr, CuI) in dioxane, DMF or NMP at 110° C. were used in the absence of a ligand.

Comdom and Palacios (R. F. P. Comdom, M. L. D. Palacios, *Synth. Commun.* 2003, 33, 921-926) used ultrasound to prepare diaryl ethers from phenols and aryl halides in a pyridine/$K_2CO_3$ system. The yields obtained were equal or superior to those reported in the literature where a high-boiling alcohol (130-170° C.) was employed as solvent.

Ren and co-workers (Y. T. Luo, J. X. Wu, R. X. Ren, *Synlett* 2003, 1734-1736) used halide-based ionic liquids as solvents, particularly 1-n-butyl-3-methylimidazolium halides (bmiX). While copper and palladium salts were assayed as catalysts, only copper salts proved successful in promoting formation of diaryl ethers. The method works well only with aryl iodides, also the high initial price of the solvent may be prohibitive.

Another, novel catalyst system consists of 20 mol % CuI, 30 mol % dimethylaminomethylphos-phonic acid derivatives as ligands and $K_2CO_3$ in toluene (Y. Jin, J. Y. Liu, Y. W. Yin, H. Fu, Y. Y. Jiang, Y. F. Zhao, *Synlett* 2006, 1564-1568).

Immobilized copper in organic-inorganic hybrid materials has been described to catalyze the Ullmann reaction of phenols and aryl iodides, bromides or chlorides (T. Miao, L. Wang, *Tetrahedron Lett.*, 2007, 48, 95-99). The protocol involves the use of DMSO as the solvent, and potassium fluoride as the base. The reactions generated the corresponding cross-coupling products in good to excellent yields. Furthermore, the silica-supported copper could be recovered and recycled by simple filtration of the reaction solution and used for 10 consecutive trials without loss of its reactivity. However, both the solvent and the base are not feasable for industrial production.

Copper impregnated charcoal catalyzes cross-couplings between aryl bromides and phenols (B. H. Lipshutz, J. B. Unger, B. R. Taft, *Org. Lett.* 2007, 9, 1089-1092). The etherifications are promoted by microwave heating.

Another new method has been provided by R.-S. Zeng and coworkers (A. Wang, R. S. Zeng, H. Q. Wei, A. Q. Jia, J. P. Zou, Chin. *J. Chem.*, 2006, 24, 1062-1065). Here, the coupling is performed with 2 mol % copper(II) chloride and 7.5 mol % 2,2'-bisimidazol in DMF at 100° C. Severe drawbacks of this protocol are the limitation to aryl iodides and the use of expensive $Cs_2CO_3$ as base.

There was still the need, therefore, to provide a process which makes it possible to prepare diaryl ethers with good yield and selectivity.

The invention is directed to a catalyst system which enables a novel procedure for the formation of diaryl ethers from aryl or heteroaryl bromides and phenols using copper salts in the presence of inexpensive 1-substituted imidazoles as additive/ligand and a alkali compound in an appropriate solvent. Under these conditions, both electron-poor and electron-rich aryl bromides react with phenols with good to excellent yield and selectivity making the method applicable on an industrial scale.

It has now be found a new process for preparing diaryl ethers of the formula (I)

  (I)

in which Ar is an aryl or substituted aryl group and Ar' is an aryl, substituted aryl or heteroaryl or substituted heteroaryl group by reacting an aryl of formula (II) or a aryloxy salt of formula (III)

  (II)

  (III), in which Ar has the same meaning as in formula (I) and R is an alkali metal, with an aryl or heteroaryl bromide of formula (IV)

  (IV)

in which Ar' has the same meaning as in formula (I), characterized in that the reaction is carried out in the presence of a copper (I) salt and a 1-substituted imidazole as catalyst system.

Ar is an aryl or substituted aryl particularly a phenyl-, substituted phenyl-, cresyl-, aniline-, bromo-aniline or biphenyl-group and Ar' is an aryl, substituted aryl, heteroaryl or substituted heteroaryl particularly a phenyl-, substituted phenyl-, cresyl-, pyridinyl or naphthyl-group.

A distinctive advantage of the catalyst system according to the invention is that multifunctional substrates such as 4-bromoaniline show no sign of self-coupling, indicating a complete selectivity of the catalytic system towards the reaction at the oxygen atom.

The use of an aryloxy salt of formula (III) like a phenolate, is preferred. Typically the alkali aryloxy salt of formula (III) such as lithium, sodium or potassium aryloxy salt is prepared in situ. The alkali compound employed for preparing the aryloxy salt of formula (III) is preferably an alkali metal hydroxide or alkoxide like sodium hydroxide, potassium hydroxide or sodium methylate, much suitable an alkali salt of weak organic acids like sodium acetate, sodium carbonate, potassium carbonate, cesium carbonate, or sodium bicarbonate.

One compound of the catalyst used in our invention is a copper (I) salt such as CuBr, CuF, CuCN, CuI, CuCl or $Cu_2O$. Preferred is CuI or CuCl. The salt may be added in amounts of 0.01 mol-% to 100 mol-% calculated from the amount of the compound of formula (IV). Preferably the salt is added in an amount of 1 mol-% to 10 mol-%.

As second compound of the catalyst system is a 1-substituted imidazole used, wherein the substituant is an alkyl, phenyl, alkenyl or acyl group, like 1-Methylmidazole, 1-Benzylimidazol, 1-Phenylimidazol, 1-Acetylimidazol, more preferably 1-Butylimidazole. The catalyst is added in amounts of 1 mol-% to 500 mol-% or could be used as solvent for the reaction, preferably the catalyst as added in amounts of 50 mol-% to 200 mol-%, calculated from the amount of the compound of formula (IV).

The preferred reaction temperature is comprised between 60° C. and 200° C., more preferably between 100° C. and 140° C.

In general the reactions are carried out in an appropriate solvent, including aromatic hydrocarbons like toluene, xylenes, mesitylene, chlorbenzene, dichlorbenzene. As mentioned above, the ligand used in the reaction could also be used as solvent for example 1-Butylimidazole.

In summary, the invention describes the application of a new catalyst system for the formation of diaryl ethers from aryl or heteroaryl bromides and phenols using copper salts in the presence of 1-substituted imidazoles as additive/ligand.

EXAMPLES

TABLE 1

The following examples are presented as illustrative of the present invention, but is not limiting of the copper/1-alkylimidazole-catalyzed diaryl ether synthesis

| entry | aryl bromide | phenol | Product | T [° C.] | metal | conversion [%][a] | yield [%][a] |
|---|---|---|---|---|---|---|---|
| 1[b] | 4-bromo-2,6-diisopropylaniline | phenol | 4-phenoxy-2,6-diisopropylaniline | 120 | CuCl (5%) | 98 | 99 (isol. 94) |
| 2 | 2-bromotoluene | o-cresol | bis(2-methylphenyl) ether | 120 | CuCl | 95 | 87 |
| 3 | 2-bromoanisole | o-cresol | 2-methoxyphenyl 2-methylphenyl ether | 120 | CuCl | 78 | 54 |
| 4 | 1-bromonaphthalene | o-cresol | 1-(2-methylphenoxy)naphthalene | 120 | CuCl | >99 | 89 |
| 5 | 2-bromo-1,3-dimethylbenzene | o-cresol | 2,6-dimethylphenyl 2-methylphenyl ether | 140 | CuI | 88 | 75 |
| 6 | 4-bromonitrobenzene | o-cresol | 4-nitrophenyl 2-methylphenyl ether | 120 | CuCl | >99 | >99 |
| 7 | 2-bromopyridine | o-cresol | 2-(2-methylphenoxy)pyridine | 120 | CuCl | >99 | >99 |
| 8 | 4-bromoaniline | o-cresol | 4-(2-methylphenoxy)aniline | 120 | CuCl | >99 | 93 |
| 9 | 4-bromoacetanilide | o-cresol | 4-(2-methylphenoxy)acetanilide | 120 | CuCl | >99 | 85 |

TABLE 1-continued
The following examples are presented as illustrative of the present invention, but is not limiting of the copper/1-alkylimidazole-catalyzed diaryl ether synthesis
| entry | aryl bromide | phenol | Product | T [° C.] | metal | conversion [%][a] | yield [%][a] |
|---|---|---|---|---|---|---|---|
| 10 | 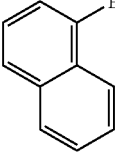 | 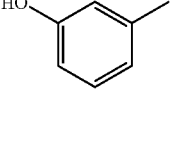 | 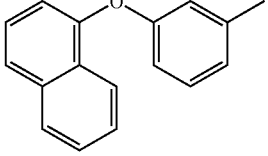 | 120 | CuCl | 84 | 84 |
| 11 | 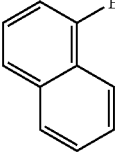 | 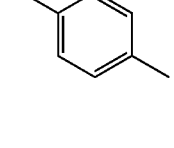 | 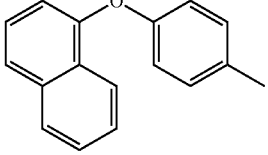 | 120 | CuCl | 89 | 85 |
| 12 | 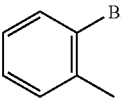 | 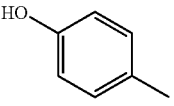 | 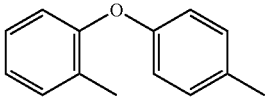 | 120 | CuCl | 86 | 84 |
| 13 | 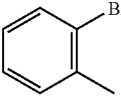 | 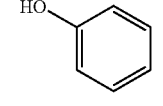 | 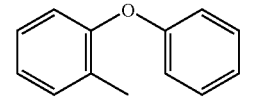 | 140 | CuI | 99 | 96 |
| 14 | 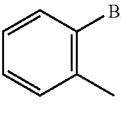 | 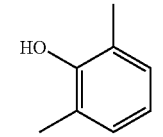 | 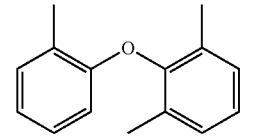 | 140 | CuI | 46 | 49 |
| 15 | 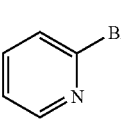 | 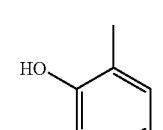 | 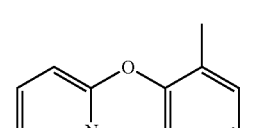 | 120 | CuCl | 100 | 95 |
| 16 | 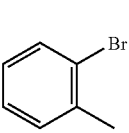 | 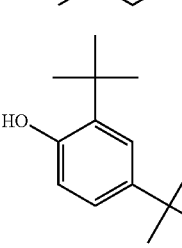 | 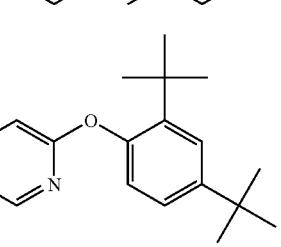 | 140 | CuI | 93 | 87 |
| 17 | 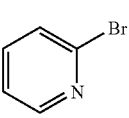 | 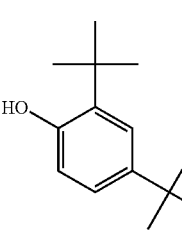 | 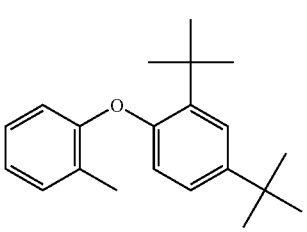 | 120 | CuCl | >99 | >99 |
| 18 | 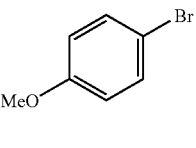 | 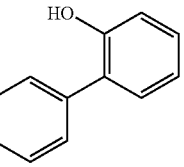 | 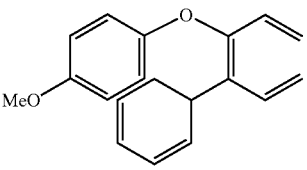 | 120 | CuCl | 74 | 78 |

General reaction conditions: 2 mmol aryl bromide, 2.4 mmol hydroxybenzene, 10 mol % metal precursor, 200 mol % $K_2CO_3$, 50 mol % 1-butylimidazole, 2 mL toluene, 200 μL internal standard (tetradecane), 16 h at temperature given, in a pressure tube under argon. [a]All percentages relative to the aryl bromide. [b]ligand=1-methylimidazole.

Example 1

Synthesis of 2,6-diisopropyl-4-phenoxyaniline (table 1, entry 1): To 32.4 g (0.234 mol) $K_2CO_3$, 0.58 g (5.8 mmol) CuCl, 13.2 g (0.14 mol) phenol, and 30 g (0.117 mol) 4-bromo-2,6-di-iso-propylaniline 2 in a 250 mL three-necked bulb with argon inlet, reflux condenser and stopper 4.7 mL (58 mmol) 1-methylimidazole and 100 mL o-xylene were added under argon atmosphere. The mixture was stirred and heated to 140° C., until thin layer chromatography (eluent toluene) showed no residual starting material 4-bromo-2,6-di-iso-propylaniline (ca. 30 h). After cooling, water and diethyl ether were added, the organic phase was washed with 10% $K_2CO_3$ solution, water and brine and dried over $Na_2SO_4$. After evaporation of the solvents, an aliquot part of the dark oily material was filtered through a short silica gel plug with toluene as solvent to give, after removal of the solvent and drying in vacuum, a dark solid. The purity is determined to 95% by gc, The calculated yield is 99%

MS (m/z, (intensity)): 269 (100), 254 (97), 146 (10), 134 (7), 77 (10).
$^1$H (CDCl$_3$. 400 MHz, 300K): 7.27 (m, 2H); 6.99 (m, 1H); 6.92 (m, 2H); 6.77 (s, 2H); 3.62 (bs, 2H, NH$_2$); 2.94 (hept., 2H, CH(CH$_3$)$_2$); 1.24 (d, 12H, CH(CH$_3$)$_2$). $^{13}$C (CDCl$_3$. 100 MHz, 300K): 159.21; 148.30; 136.57; 134.32; 129.45; 121.61; 116.75; 115.08; 28.14; 22.39.

Example 2

Synthesis of 1-(o-tolyloxy)naphthalene (table 1, entry 4): 278 μL (2 mmol) 1-bromonaphthaline, 20 mg (0.2 mmol) copper(I) chloride, 550 mg (4 mmol) potassium carbonate, 260 mg (2.4 mmol) o-cresol, 130 μL 1-butylimidazole, 2 mL toluene and 200 μL internal standard (tetradecane) were added to an Ace pressure tube under argon and heated to 120° C. for 16 h. After cooling, water and diethyl ether were added, the organic phase was washed with 10% $K_2CO_3$ solution, water and brine and dried over $Na_2SO_4$. GC analysis of the organic phase showed a yield of 89%. After evaporation of the solvents, the dark brown oil was submitted to column chromatography over silica gel, eluent light petroleum. 0.38 g of colourless oil was recovered (81% isolated yield). The substance was identified by gc/ms and nmr spectroscopy.

MS (m/z, (intensity)): 234 (100), 129 (20), 191 (8), 128 (77), 115 (26).
$^1$H (CDCl$_3$. 300 MHz, 300K): 8.32 (m, 1H); 7.85 (m, 1H); 7.52 (m, 3H); 7.30 (m, 2H); 7.13 (bm, 2H); 6.91 (m, 1H); 6.67 (m, 1H); 2.29 (s, 3H).
$^{13}$C (CDCl$_3$. 75 MHz, 300K): 154.83; 153.74; 134.93; 131.56; 129.92; 127.75; 127.30; 126.64; 126.16; 125.86; 125.80; 124.12; 122.28; 122.11; 119.78; 110.55; 16.21.

Example 3

Synthesis of 2-(2,6-dimethylphenoxy)pyridine (table 1, entry 15): 191 μL (2 mmol) 2-bromopyridine, 20 mg (0.2 mmol) copper(I) chloride, 550 mg (4 mmol) potassium carbonate, 293 mg (2.4 mmol) 2,6-dimethylphenole, 130 μL 1-butylimidazole, 2 mL toluene and 200 μL internal standard (tetradecane) were added to an Ace pressure tube under argon and heated to 120° C. for 16 h. After cooling, water and diethyl ether were added, the organic phase was washed with 10% $K_2CO_3$ solution, water and brine and dried over $Na_2SO_4$. GC analysis of the organic phase showed a yield of 95%. After evaporation of the solvents, the dark brown oil was submitted to column chromatography over silica gel, mixtures of light petroleum and ethyl acetate were used as eluent. 0.32 g of light yellow solid was recovered (80% isolated yield). The substance was identified by gc/ms and nmr spectroscopy.

MS (m/z, (intensity)): 199 (65), 184 (61), 182 (100), 167 (14), 78 (17).
$^1$H (CDCl$_3$. 300 MHz, 300K): 8.15 (m, 1H); 7.64 (m, 1H); 7.03-7.13 (m, 3H); 6.92 (m, 1H); 6.80 (m, 1H); 2.12 (s, 6H).
$^{13}$C (CDCl$_3$. 75 MHz, 300K): 163.23; 150.38; 148.03; 139.38; 131.17; 128.77; 125.38; 117.64; 109.66; 16.59.

The invention claimed is:

1. Process for preparing diaryl ethers of the formula (I)

Ar—O—Ar'  (I)

in which Ar is an aryl or substituted aryl group and Ar' is an aryl, substituted aryl, heteroaryl or substituted heteroaryl group
by reacting an aryl of formula (II) or a an aryloxy salt of formula (III)

Ar—OH  (II)

Ar—OR  (III)

in which Ar has the same meaning as in formula (I) and R is an alkali metal,
with an aryl or heteroaryl bromide of formula (IV)

Ar'—Br  (IV)

in which Ar' has the same meaning as in formula (I),
characterized in that the reaction is carried out in the presence of a copper(I)salt and a 1-alkyl-substituted imidazole as catalyst system.

2. Process according to claim 1 characterized in that the copper(I)salt is CuBr, CuF, CuI, CuCl or $Cu_2O$.

3. Process according to claim 1 characterized in that the copper(I)salt is added in an amount of 0.01 mol-% to 100 mol-% calculated from the amount of the compound of formula (IV).

4. Process according to claim 1, characterized that the aryloxy salt of formula (III) is prepared in situ by adding an alkali compound to the reaction mixture.

5. Process according to claim 1, characterized in that the alkali compound is an alkali metal hydroxide or metal alkoxide.

6. Process according to claim 1 characterized in that the reaction is carried out at a reaction temperature between 60 and 200° C.

7. Process according to claim 1 characterized in that the reaction is carried out in 1-Butylimidazole as solvent.

8. Process according to claim 1 characterized in that Ar is a phenyl, substituted phenyl, cresyl- or biphenyl-group and Ar' is phenyl, substituted phenyl, aniline, cresyl, pyridinyl or naphthyl-group.

9. A method for using a copper(I)salt/1-substituted imidazole system as catalyst system comprising using the catalyst system for the catalytic synthesis of diaryl ethers.

10. The process according to claim 1 wherein the 1-alkyl-substituted imidazole is 1-Butylimidazole.

* * * * *